(12) United States Patent
Lacey

(10) Patent No.: US 8,819,837 B2
(45) Date of Patent: Aug. 26, 2014

(54) MEDICAL AND PERSONAL DATA RETRIEVAL SYSTEM

(75) Inventor: Michael P Lacey, Pompano Beach, CA (US)

(73) Assignee: LifeQode, LLC, Menlo Park, CA (US)

(*) Notice: Subject to any disclaimer, the term of this patent is extended or adjusted under 35 U.S.C. 154(b) by 1623 days.

(21) Appl. No.: 11/536,817

(22) Filed: Sep. 29, 2006

(65) Prior Publication Data
US 2007/0074043 A1    Mar. 29, 2007

Related U.S. Application Data

(60) Provisional application No. 60/721,705, filed on Sep. 29, 2005.

(51) Int. Cl.
| G06F 21/00 | (2013.01) |
| H04L 9/32 | (2006.01) |
| G06F 19/00 | (2011.01) |

(52) U.S. Cl.
CPC ............ *G06F 19/323* (2013.01); *H04L 9/3226* (2013.01); *H04L 2209/80* (2013.01); *H04L 2209/88* (2013.01); *H04L 2209/84* (2013.01)
USPC ...................... 726/26; 713/186; 705/2; 705/3

(58) Field of Classification Search
CPC ........................................................ H04K 1/00
USPC .............. 705/2, 3; 726/26; 713/186
See application file for complete search history.

(56) References Cited

U.S. PATENT DOCUMENTS

| 4,226,036 A | 10/1980 | Krug |
| 4,249,330 A | 2/1981 | Chioffe |
| 4,984,683 A | 1/1991 | Eller |
| 5,359,798 A | 11/1994 | Pelosi |
| 5,649,381 A | 7/1997 | Studer |
| 5,877,742 A | 3/1999 | Klink |
| 6,073,106 A * | 6/2000 | Rozen et al. ...................... 705/3 |
| 6,131,090 A * | 10/2000 | Basso et al. .................... 706/23 |
| 6,155,409 A * | 12/2000 | Hettinger ........................ 206/38 |
| 6,463,185 B1 * | 10/2002 | Mori et al. ..................... 382/302 |
| 6,467,960 B1 | 10/2002 | Watson et al. |
| 6,747,561 B1 | 6/2004 | Reeves |
| 6,944,767 B1 | 9/2005 | Judson |
| 7,702,108 B2 * | 4/2010 | Amon et al. .................. 380/270 |
| 2002/0092220 A1* | 7/2002 | Mitchell ......................... 40/633 |
| 2003/0040940 A1 | 2/2003 | Nehammer |
| 2003/0182055 A1* | 9/2003 | Curatolo et al. .............. 701/207 |
| 2003/0220822 A1 | 11/2003 | Fiala et al. |
| 2004/0205067 A1* | 10/2004 | Veidung ......................... 707/10 |

(Continued)

OTHER PUBLICATIONS

PCT Search Report dated Apr. 24, 2008 of Patent Application No. PCT/US06/38041 filed Sep. 29, 2006.

(Continued)

*Primary Examiner* — Jason Lee
(74) *Attorney, Agent, or Firm* — Levine Bagade Han LLP

(57) ABSTRACT

A system for confidentially retrieving data from a person, such as by authorized personnel. One embodiment provides a data carrier item such as jewelry, having encrypted data imparted upon the item in manner that is only intelligible after being unencrypted. Such data can be encrypted and/or invisibly disposed such that the data is not identifiable by the public, but can be quickly and accurately retrieved by authorized personnel.

13 Claims, 8 Drawing Sheets

(56) References Cited

U.S. PATENT DOCUMENTS

| | | | |
|---|---|---|---|
| 2005/0006274 A1* | 1/2005 | Cox | 206/569 |
| 2005/0021369 A1* | 1/2005 | Cohen et al. | 705/2 |
| 2005/0061890 A1* | 3/2005 | Hinckley | 235/494 |
| 2006/0042139 A1* | 3/2006 | Mendes | 40/633 |

OTHER PUBLICATIONS

"MedicAlert Emblems" [retrieved on Nov. 7, 2006] Retrieved from the internet <URL: http://www.medicalert.org/Home/HomeEmblemCatalogs.aspx>.

* cited by examiner 5
10
20
25

30
35
50
60
70

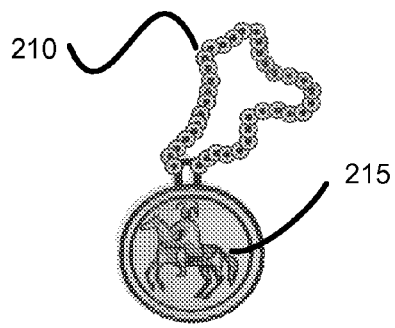
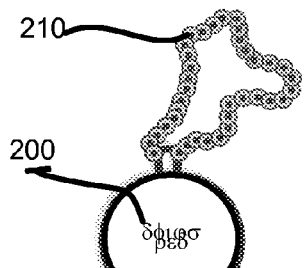
Figure 2a Figure 2b
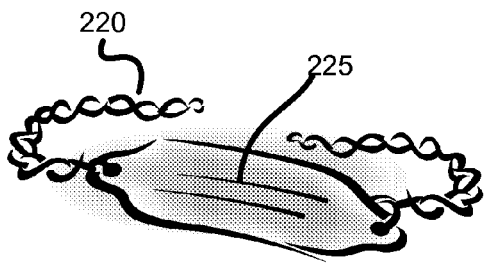
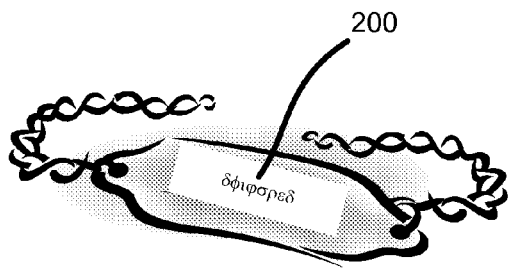
Figure 2c Figure 2d
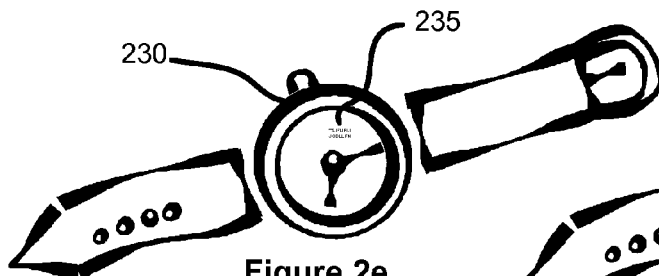
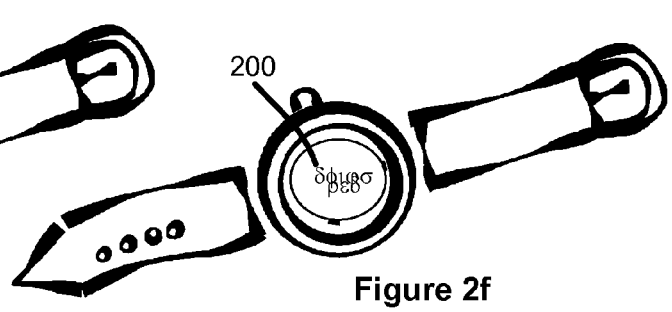
Figure 2e Figure 2f
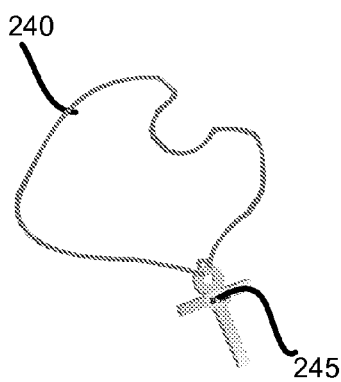
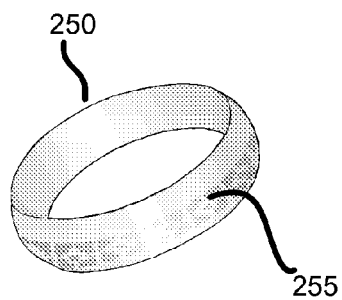
Figure 2g Figure 2h Data Storage Data Matrix Symbol Shown Complete Broken Border Solid Border

MEDICAL AND PERSONAL DATA RETRIEVAL SYSTEM

RELATED APPLICATIONS

This application claims the benefit of U.S. Provisional Applications No. 60/721,705, filed Sep. 29, 2005, and is herein incorporated in its entirety by reference.

FIELD OF THE INVENTION

The invention relates to the health care industry, and more particularly, to providing a mechanism for safely retrieving a person's medical data and personal information.

BACKGROUND OF THE INVENTION

The statistics have proven that in emergency situations, many people are given improper medial treatment due to a lack of knowledge or misunderstanding of a person's medical history. A person may be unconscious or in such a state that asking detailed medical questions would be futile. Information about a person such as allergies and diabetes could be vital to prompt and proper treatment. Emergency personnel and treating physicians may therefore lack important medical conditions of a person and the treatment may complicate matters or be fatal.

In addition to medical conditions, it is equally important to know the type of prescription medications that a person may be taking. There are a number of prescriptions that conflict such that the result could effectively cancel each other or in some instances the resulting conflict could be dangerous.

There have been many attempts to provide a patient with some mechanism to indicate important medical conditions or medications. Certain jewelry items can include limited information such as name, emergency telephone numbers and some very basic health status indicators. Not only is the amount of information limited, but it is visible to anyone, thereby making a person's confidential medical and personal data publicly available.

There are other medical data mechanisms that list certain detailed information on emergency cards. However these cards may be hidden away in a wallet or purse and it may be difficult to locate. It also may look inappropriate for emergency personnel to be digging through the wallet of an unconscious person.

Another system recognizes the confidential nature of the medical information and provides codes and/or passwords to emergency personnel and requires the emergency responders to access a third party and relay the codes or passwords in order to find out the details of the person's medical information. There would be a potentially life-threatening delay in such a process and it requires the personnel to use a form of communications that may not be accessible.

There are also some implementations that incorporate microprocessors and electronics to store the medical data and require some mechanism to interface with the stored data. Such a system adds cost and complexity as well as a power source. In addition, electronics are susceptible to damage, especially if worn on a person. There are other systems that implant medical data within the person however some consider these systems to be intrusive and undesirable.

What is needed, therefore, is some system of providing medical data to those personnel that require it. There needs to be a way to capture enough information to be useful to the end-user and not merely contact data. The data should be in a format that maintains the confidential nature of the medical data and not easily discernable to everyone. And, the data should be presented in a manner that is easy to locate and easy to find.

SUMMARY OF THE INVENTION

A general embodiment of the present invention provides a jewelry or similar item having confidential data, such as personal and medical data, imparted upon the item in manner that is only intelligible to personnel having appropriate equipment and authorization.

One embodiment of the invention is a system for obtaining personal information about a distressed person, including identifying a data carrier coupled about the distressed person by an authorized party, wherein the data carrier contains encrypted data, and wherein the encrypted data represents at least some of the personal information, retrieving the encrypted data from the data carrier by the authorized party, processing the encrypted data on a computing device and unencrypting at least a portion of the encrypted data into unencrypted information, and communicating the unencrypted information to the authorized party.

A further aspect includes wherein retrieving is performed by a scanner capable of reading at least one of data matrix, nanoengraving, magnetic trace, and invisible ink.

According to one embodiment, the data carrier is selected from at least one of the group consisting of: card, watch, pendant, broach, necklace, medallion, earrings, eyeglasses, contact lens, body piercing item, ring, and bracelet.

An additional feature is wherein the portion of the encrypted data available is predefined.

In one embodiment, communicating over a network to retrieve supplemental information about the distressed person.

The step of identifying may include at least one of the group consisting of: data carrier logo, data carrier shape, data carrier coloration, data carrier design, data carrier textual message, invisible ink on the data carrier, magnetic traces on the data carrier, notification by an alerting company, and decal on a vehicle, residence or person.

Another aspect includes wherein the communicating includes at least one of displaying the information, audio output of the information, and audio/visual output of the information.

A further features is wherein the personal information includes at least one of a name, social security number, age, sex, date of birth, address, telephone number, religion, emergency contact information, physician information, allergies, prescriptions, blood type, medical conditions, implant details, health insurance provider, and health insurance plan.

Another embodiment includes wherein the computing device is a laptop computer, tablet PC, cell phone, and personal digital assistant (PDA).

A further aspect includes wherein the computing device is local to the party.

A method for communicating confidential information about a distressed person, including encrypting the confidential information into encrypted data, affixing the encrypted data onto a data carrier, wherein the data carrier is coupled about the person, providing a mechanism for identifying the data carrier, in a distressed situation, locating the data carrier by an authorized party, scanning the data carrier by the authorized party and retrieving the encrypted data, processing the encrypted data into an authorized portion of confidential information, displaying the authorized portion of confidential information in a graphical user interface.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

FIG. 2a-2h illustrates examples of the data carrier configured in accordance with one embodiment of the present invention.

DETAILED DESCRIPTION

Figure 1A:
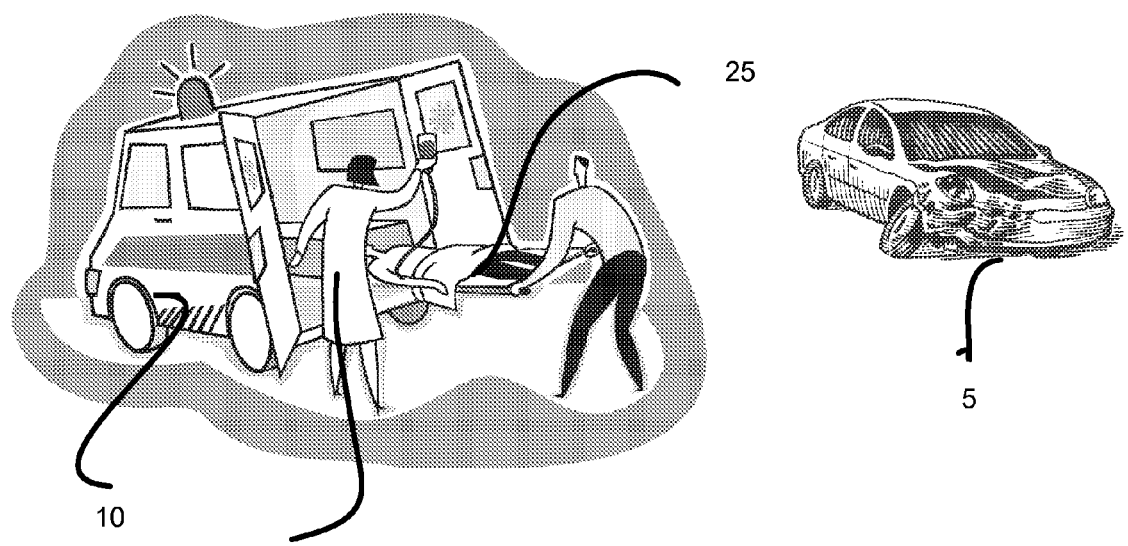
FIG. 1a illustrates an accident scene showing an injured person being attended to by emergency personnel.
Figure 1B:
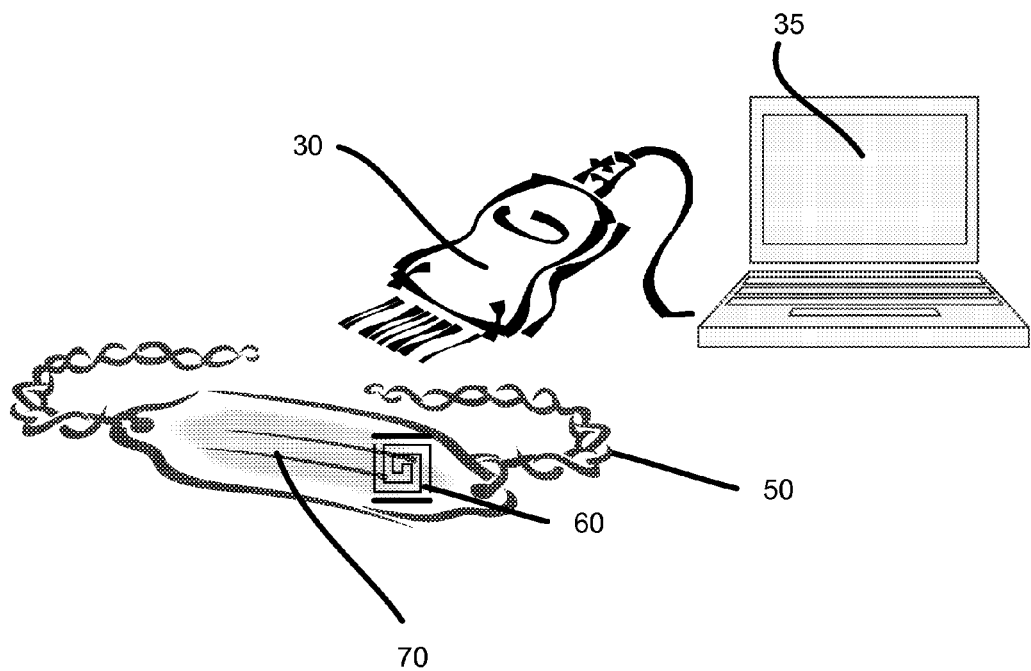
FIG. 1b shows an item from the injured person bearing encrypted information that is read by a handheld scanner coupled to a computing device, according to one embodiment of the invention.

Referring to FIG. 1a and FIG. 1b an emergency scene is depicted wherein a car accident 5 is shown as one example of a situation where the present invention is applicable. In this example, at the scene of an accident a person 25 is distressed or injured and possibly unconscious or otherwise not communicative in an intelligent fashion. An emergency vehicle 10 at the accident scene would bring EMS or other medical personnel 20. The medical personnel 20 would carry or have available at the vehicle 10, a means for retrieving encrypted data 70 from a data carrier 50 on the injured person 25.

The emergency personnel include any persons that would normally attend to distressed persons and have the scanning equipment. This would include at least EMS, fire and rescue, police, and those in the field of attending to distressed persons such as hospitals and clinics.

While the description of FIG. 1 describes injury-related emergency situations, other embodiment relates to less critical situations for persons that are unable or unwilling to provide adequate information, which are defined herein as distressed persons. Children, elderly, those with medical conditions or under medication are sometimes unable to give required information in a timely manner, whether it is an emergency situation or a non-emergency situation, such conditions are referred to herein as distressed situations. In situations that require such information, the present invention allows an authorized user to quickly obtain the data. Such authorized personnel can include at least school personnel such as a school nurse, nurses and physicians, and office personnel. Nursing homes, senior housing facilities, schools, and theme parks are some of the institutions that would benefit from the present invention.

A further embodiment relates to military, corporate and security applications. The present invention does not require the transmission of data via wireless or wired networks and thus provides an attractive alternative to such systems. Thus, the present invention is not limited to only extracting medical data from distressed persons and other embodiments are within the scope of the present invention.

An additional embodiment relates to correction facilities, prisons, detention centers, and related holding facilities wherein the data carrier can be affixed to a person such that it can only be removed by authorized personnel. Such ankle bracelets are currently used for home detention. The data carrier of the present invention can be integrated onto the non-removable data carrier and allow for quick and simple identification of such persons.

According to one embodiment, a scanner 30 is coupled to a computing device 35, such as a laptop computer, having a screen display, input mechanisms such as a mouse and/or keyboard, and attachable peripheral devices such as the scanner 30. It should be readily apparent that the present invention is not limited to a laptop computer and various computing device may be implemented such as tablet PC's, PalmPilots, personal digital assistants (PDAs), cell phones, and similar devices having some processing capability and some mechanism to input the encrypted information 70. According to the depicted embodiment, the scanner 30 is a separate component that is wired to the computing device 35. The scanner 30 can also be a wireless device wherein the scanner 30 would read the encrypted data 70 and transmit to the computing device 35 for subsequent processing. As detailed herein, another variation includes the scanner being a self-contained unit having a microprocessor, display screen, and power source built into the unit for scanning, processing and displaying the data.

An algorithm is used to securely extract the person's information from the encrypted data carrier 50. The person's information may include, for example, such details as name, date of birth, address, emergency contact information, primary care physicians, allergies, and medications. There is ample room for any helpful and useful information to be securely contained on a data carrier 50 and safely and securely extracted by the scanner 30 and processed/displayed by the computing device 35 to the authorized personnel 20. According to one embodiment, the algorithm is capable of decrypting any of the various methods used to encrypt the information on the data carrier.

The extracted information can be displayed or communicated in several ways. For example, the data can be displayed on a display screen of a laptop, PDA and other computing device. The information can also be processed and communicated in an audible format or some combination of audio/visual.

In one variation, health insurance information may be securely stored on the data carrier 50 allowing the health insurance provider information to be associated immediately with the injured person 25. As detailed herein, the processing system can be established with certain levels of security such that certain personnel may only retrieve a portion of the encrypted data.

A further variation employs wireless technology such that the scanner system 30, whether having a scanner coupled to a computing device or a self-contained scanner, the scanned information is transmitted to another location. The scanned information can be processed at the other location, such as the ambulance, hospital or other database provider, and the secure information would be transmitted back to the scene of the accident for the authorized personnel 20.

As demonstrated in recent events such as hurricane Katrina and the terrorist attacks of the World Trade Center, communications are disrupted. Unlike other systems that require a link to a centralized database to ascertain the required information, the present invention provides for processing of the encrypted data on-site and immediately obtains the data. The processing can be done on-site since the decoding algorithm would typically be resident on the computing device. The local transmission of the data, for example, from a wireless reader to a processing unit still does not employ a satellite or network data transmission to a database to identify the person and then a re-transmission back to the end-user with the requested information. The processing unit processes the encrypted data without such a retrieval mechanism. As noted herein, the computing device can be local to the authorized party such that it is either in-hand or located nearby such as in the emergency vehicle.

A further embodiment of the invention is an alerting mechanism, such as a small icon or symbol 60 on the data carrier 50, alerting medical personnel that the article is encrypted with personal and health information. In another embodiment, the data carrier system employs existing articles of the person and the medical and personal information is affixed to the article. The existing article can be engraved or embossed with the data as well as the logo. Alternatively, the data and logo can be placed onto adhesive backed materials and affixed to the existing article.

The data carrier 50 in one embodiment is a piece of jewelry, although it could be configured as any item capable of being engraved or printed with coded data 70. One embodiment employs metals such as sterling silver and gold providing aesthetic beauty along with the useful information.

Referring to FIG. 2a-FIG. 2h, various data carriers are illustrated. The data carriers can be new articles that would be obtained by an individual and the medical and/or personal information would be affixed to the article. In other embodiments, the encrypted data is affixed to existing articles wherein the engraving/printing can be done at authorized centers or processed at authorized centers and shipped. By way of one example, if a person wanted to place the encrypted data on a pocket watch, there can be a form or on-line screen to obtain the desired information. The item would be engraved and shipped accordingly.

Referring to the necklace 210 with the medallion 215 in FIGS. 2a and 2b the front and back perspectives are shown. In one embodiment, the front of the medallion 215 includes a logo or symbol identifying that the bracelet has data information however it may also be just decorative. Such encrypted information 200 is depicted on FIG. 2b on the back of the medallion 215. In this embodiment the encrypted data 215 is visible, although unintelligible without the scanner and processing by the algorithm. While the front is shown to be decorative, it is also within the scope of the invention to have the encrypted data be depicted on the front thereby easily identifying the data carrier.

FIGS. 2c and 2d show the data carrier as a bracelet 220 that can be for example, a wrist or ankle bracelet. One side of the bracelet 225 can be ornamental and/or it can identify itself as a data carrier by a symbol, logo, or other identifier. On the other side of the bracelet can be the encrypted data 200.

A wrist watch 230 is shown in FIGS. 2e and 2f, wherein on the display side there is an engraving done using nanotechnology. In this embodiment, the watch 230 can be a designated data carrier watch that is easily identifiable by others wherein the encrypted data 235 requires a reader to discern the data. As shown in FIG. 2f, the encrypted data 200 can be affixed to the back surface of the watch 230.

Other data carriers shown in FIG. 2g include religious items such as a cross 240 that can include the encrypted data 245 which may be visible or not visible, such as printed/engraved by nanotechnology. A further data carrier includes a ring 250 wherein the encrypted data 255 can be disposed on the outer surface. The ring itself can be a specially designed ring 250 such that it serves as an identifier. The data itself can be visible, or it can be invisible such as magnetic traces, invisible ink, or nanoengravings.

According to one embodiment, the data carrier has some form of identifier so that emergency personnel can easily locate the carrier. For example, the data carrier can have a symbol, coloration, design, shape, logo, or be configured in such manner as to be distinguishable. In one embodiment the data carrier is worn in a certain manner that enables identification. It is within the scope of the invention for the data carrier to be a new social trend akin to the Livestrong® bracelets. With proper training, authorized persons should be able to identify the data carrier either by viewing the encrypted data or by identifying some indicator that it is a data carrier.

The present invention tries to incorporate the encrypted data into items that are normally carried or worn by people, such as jewelry and watches. Examples of data carriers include at least a nametag, bracelet, pendant, necklace, medallion, cross, watch, chokers, ring, medal, charm bracelet, and broach. Other possible data carriers include eyeglasses, earrings, body piercing items, and contact lenses. A temporary data carrier is useful, for example, at large theme parks where lost children can be quickly identified and reunited with parents. While there are numerous child locater systems, most are complicated systems employing sophisticated electronics that rely upon satellite and wireless technology that extracts data from a central database. And, it requires the user to have a specific electronic device that is worn, ingested or embedded on the person.

The data carrier in one embodiment will hold an individual's personal details and medical information, collectively called personal information, including, but not limited to, verifying descriptor, vital information, medical conditions and history, current medications, primary care physician, medical insurance carrier, and emergency contact information. There are certain advantages to having the data readily accessible on the person as opposed to being hidden or stored somewhere on the person. However, the confidential personal and medical information should not be readily discernable to others.

Figure 3:
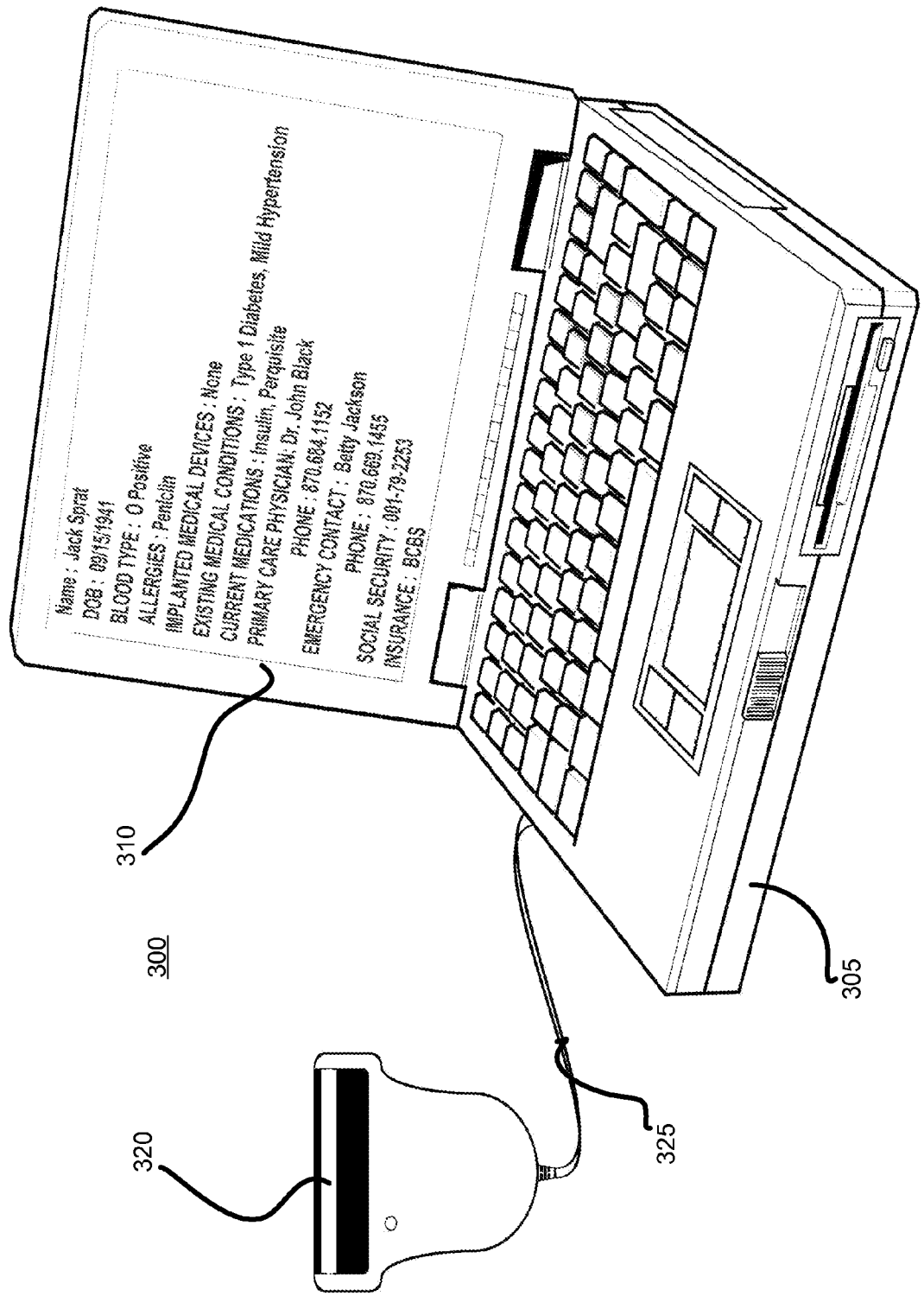
FIG. 3 shows an exploded view of a computing device and scanner with a graphical user interface according to one embodiment of the invention.

FIG. 3 shows one embodiment of the scanning system 300 including the scanner head 320 coupled by a wire 325 to a computing device 305, which in this example is a laptop. In this wired version, the scanner head can be lightweight and inexpensive as the electronics and power are on the computing device. The wire 325 should be long enough to provide access to a person which depends upon the intended usage. The display 310 shows an example of typical fields of data that can be extracted and read by the system 300. Such fields include name, date of birth, blood type, allergies, implants, existing medical conditions, medications, physician, physician contact details, emergency contact, social security number and health care provider.

According to one embodiment of the invention, there are several levels of information that can be extracted from the data carrier. The algorithm resident on the computing device will only be able to unencrypt the portion of information relevant to that person. For example, an EMS may be authorized to obtain all the medical data but would be unable to access certain personal data such as social security number and health care details. A health care administration person may be able to access certain details such as social security and health plan coverage but would not be able to access certain medical history. Similarly, other personal, medical and financial data on a single data carrier can have usage restrictions based on the algorithm on the computing device. The algorithm itself can be installed or replaced by another algorithm such as by a download. According to one embodiment the authorization levels are predefined and established on the computing device that performs the scanning process. There may be multiple levels on a single system with some security mechanism such as password or biometric to ensure proper authorization.

FIGS. 4a-d illustrates one embodiment for the encrypted data 420, wherein a data matrix method of data encoding is described. The data matrix methodology is one of the smallest and most dependable barcode symbologies. A data matrix is an area efficient 2D (two dimensional) barcode symbology that uses a unique perimeter pattern which helps the barcode scanner determine the cell locations. The cells are made up of square modules and it can encode letters, numbers, text and actual bytes of data. The data matrix technology can encode just about anything including text characters, unicode characters and photos. It is commonly used to encode data from a few digits to several hundred digits. The encoding and decoding process of data matrix is relatively complex and includes sophisticated error correction. There are various standards committees and guidelines such as ECC200 from the ANSI/AIM BC11 and ISO/IEC 16022 specifications. The latest technology supports advanced encoding and error checking with error correction algorithms such as Reed Solomon. In certain embodiment these algorithms allow the recognition of barcodes that are up to 60% damaged.

There are a number of companies employing encoding/decoding technologies and the data matrix in this embodiment is a 2-dimensional barcode that can be either engraved or printed on an object and contains large amounts of information in a relatively small area. In the case where the data carrier is jewelry, the information can be laser engraved in an inconspicuous location, typically on the backside, in the form of a data matrix (2-dimensional barcode). The amount of information required for an individual will determine the size or particular style of jewelry appropriate for the individual.

Figure 4C:
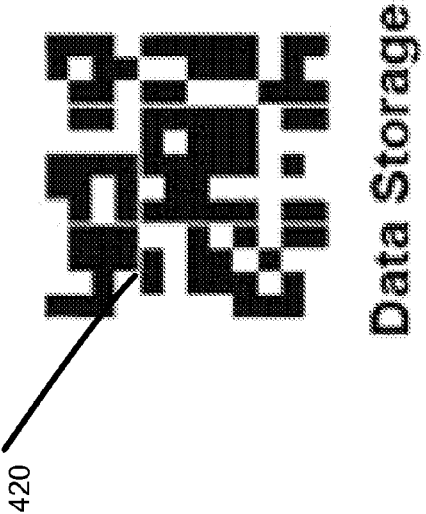
FIG. 4a-d shows various perspective views of the formation of the data carrier configured in accordance with one embodiment of the present invention.
Figure 4D:
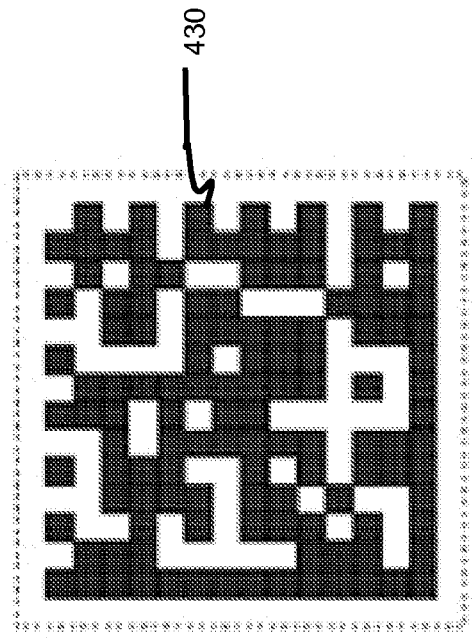
Figure 4B:
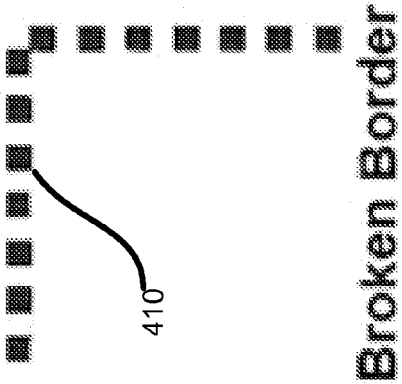
Figure 4A:
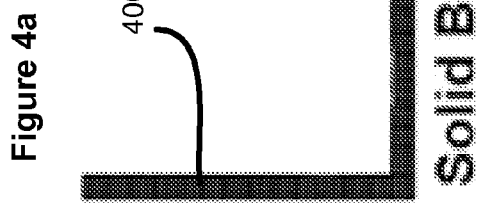

Referring again to FIG. 4a-4d, the information is digitized into square modules, or cells 420, and can be placed in discrete locations within the matrix to facilitate scanning. Placing the data into discrete locations is used to improve the speed of acquisition and the accuracy of retrieval of the data as there are sequences with respect to the data points, much as in Code 39 (standard barcodes), where the line spacing, width and surrounding "quiet zones" are used for recognition. There can be border patterns 400, 410 used to help identify the information contained in the cells 420. This makes it an extremely efficient 2-dimensional barcode using unique perimeter patterns 400, 410 to help the scanner determine cell locations. In essence, the borders define the data storage area, serving as "anchors" or reference points for the scanning system. The solid border 400 shown in FIG. 4a and the broken border 410 in FIG. 4b illustrate some of the perimeter patterns that can be employed to aid in the scanner capture and interpretation of the data from the cells 420. FIG. 4d shows a complete representation of the data matrix including the perimeter patterns 400, 410 and data 420.

As the information can be vital, it is important that the encrypted data be accurately retrieved. In the data matrix embodiment, misreading of information occurs in only one (1) in 10.5 million scans, and is capable of encoding anywhere from a few digits up to several hundred digits in a single matrix. The encoding and decoding of the data matrix is complex, but with error correction the data information can be accurately read with up to 60% damage to the cells in the matrix.

There are various engraving processes used for forming encrypted data on articles. As noted herein, the encrypted data can be formed on new articles such as bracelets and watches and also on existing articles. One embodiment is a secure Web based interface for obtaining and updating the person's medical data. The articles can be engraved with the data and shipped to the person for the ordering of new articles. Updating information or encoding information on a person's existing articles can be done via shipping to an authorized representative that has access to the secure database.

The engraving process can be performed by a computer-controlled laser such as a YAG (Yttrium Aluminum Garnet) or Nd:YAG (Neodymium doped YAG) lasers, which are very high powered solid-state lasers capable of engraving on a wide variety of materials, such as steel, aluminum, platinum, gold, silver, plastics, glass. The person's information can be downloaded into a computer by scanning an OCR (Optical Character Recognition) form, electronically imported from another source or program, or even manually entered. The data computer, which could also be the laser controller, will encrypt the information and reformat it into an encrypted format such as an engravable I.D. matrix. If the data compilation computer is not the laser controller, the formatted file can be transferred to the laser controller either through some type of network connection or removable storage media. The item to be engraved will then be positioned for engraving by the laser. There are a number of lasers and related technology that all within the scope of the present invention.

Alternately, if the item to be marked is not suitable for YAG engraving, for example certain flexible materials such as paper, labels, or adhesive tapes, a laser printer of sufficient print resolution may be substituted as the marking instrument. Substrate suitability for the application with respect to durability and contrast is one consideration for employing such materials.

A further printing method employs an ink that is not visible by excitation in the visible spectrum which is substituted for a visible ink. This "invisible ink" requires excitation by either UV (ultraviolet), heat (thermochromic) or IR (infrared) excitation in order to be scanned and read. This method expands the acceptance of the system to a great number of items not presently under consideration for aesthetic reasons. For example, the logo or identifier can be designated in visible ink so that the personnel would know that the medical information is inscribed in the invisible ink and the location of the data can be established by the location of the logo. Regardless of the method employed, items will be scanned after marking to ensure the data retrieval system functions properly and there are no errors in the data.

Engraving/marking of existing jewelry articles requires specific procedures and methods such as liability for damage to heirlooms or precious personal items. The "invisible ink" or other non-visible system may be preferable in these items. Applying the data to existing jewelry marking requires a scheme for being able to apply an acceptable, inconspicuous indication that the item contains medical information.

In another embodiment, the data carrier article utilizes an application of magnetic material to generate the data cells and create a discrete magnetic response in a similar fashion to the optical characterization described herein. The encrypted portion therefore might not be visible, and would not detract from any aesthetic qualities. A scanner/reader reads the magnetic pattern and the data is unencrypted by the algorithm as described herein.

The magnetically encoding traces can be subdivided into high and low coercivity, wherein low coercivity (soft magnets), allow the magnetization and reading of the magnetic traces or cells. High coercivity (Hard magnets), such as those used on credit cards, negate the requirement for a reader that generates a field.

A further embodiment pertains to the use of nanotechnology. The data carrier can be engraved or printed using nanoscale elements to generate the data cells. Nanoengravers and nanoprinting devices can affix a data carrier having an extremely small footprint yet contain a significant amount of detail. A nanoreader would extract the encrypted data from the data carrier. The printing/engraving using nanotechnology allows all suitable data to be placed in an extremely small area such as the size of a pinhead. This expands the field of the data carrier to very small items that may be carried by a person in normal activity and also be recognized as a data carrier. For example, earrings, body piercing items, and even contact lenses can be employed in this fashion to contain the nano-coded data that is then extracted by the nanoreader. Retrieving the encrypted nanotechnology data can include scanning the data carrier with a lens array or other magnification system.

The code will typically contain the date when the information was collected, giving some relative indication to healthcare personnel as to the reliability of accuracy and currency of the information. The present system may opt to query clients on a periodic basis either electronically, through telephone interviews, or postal mailings, in order to update medical information. However, maintaining up-to-date information will largely be the responsibility of the subscriber to timely report changes in medical information. As changes are required to information for existing clients the present invention will offer a means for customers to receive an expedited replacement or corrected data carrier.

Figure 5:
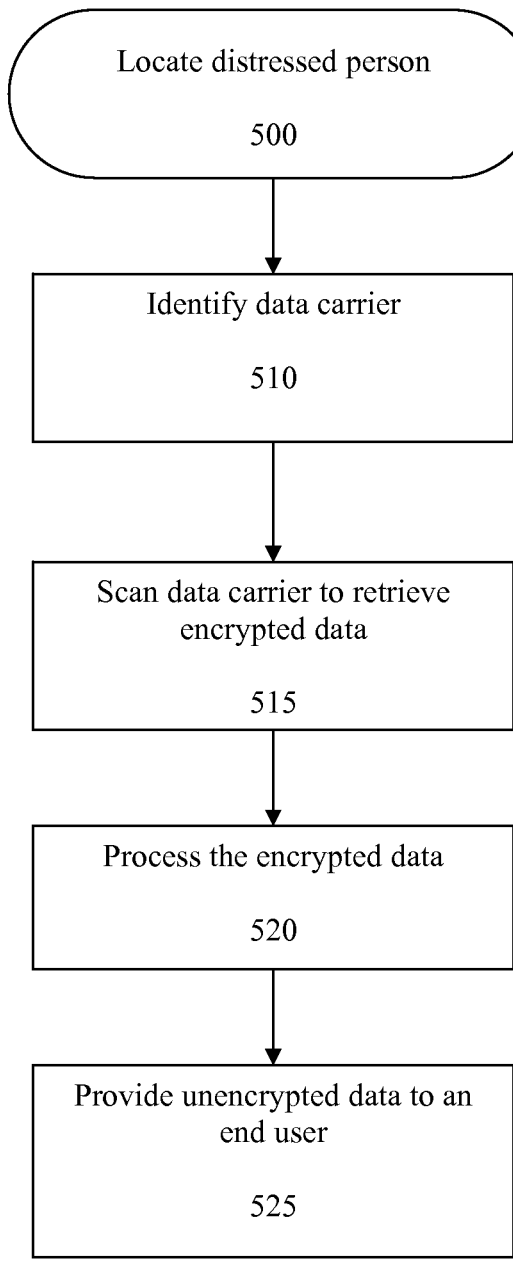
FIG. 5 depicts the processing of the system configured in accordance with one embodiment of the present invention.

One embodiment of the system processing is depicted in FIG. 5, in an example that commences with the location of a distressed person such as at the arrival of medical personnel at an emergency situation or of locating an elderly person or child. The personnel needs to identify the data carrier 510, such as by looking for the logo, symbol or other identifier as detailed herein.

There are a variety of mechanisms to alert the staff, professionals and emergency personnel that a person has encrypted medical data according to the teachings of the present invention. Firstly, a conscious patient can verbally inform personnel of the data carrier. The present invention can provide alerting decals with an appropriate logo that is affixed in a specific location on a vehicle or residence to indicate the medical data is on the patient. The logo can also be engraved or affixed to the data carrier such as a bracelet. Furthermore, the present system can be deployed having relationships with alerting and safety companies such as Onstar® for vehicles and A.D.T.® and similar home monitoring companies, which alert emergency personnel of medical emergencies at the home or in the vehicle. These various resources increase the likelihood that a person that is rendered unconscious or incoherent can have their medical data properly communicated to those personnel that respond.

Once the personnel locate the data carrier, the data carrier is scanned in order to retrieve the encrypted information 515. The scanned data is then processed by an algorithm that processes/unencrypts 520 at least some of the encrypted scanned data according to the authorization level of the user. Once the data retrieved, it is communicated to the user 525 such as by a display on the screen, audibly or in print form. The user can promptly begin to assist the distressed person armed with information about the person, including allergy information and other pertinent data.

Data retrieval in one embodiment utilizes a 2-dimensional barcode scanner. This can be a handheld laser reader designed to capture the information in the matrix and convert it to a readable text format such as ASCII or C40. The C40 system is used to encode data that mainly contains numeric and upper case characters, wherein the C40 encodes three alphanumeric data characters into two bytes. Compared to other barcode types, the Data Matrix is approximately 30 times smaller than a Code 39 barcode representing the same data. There are various other data encryption types as known by those skilled in the art.

The data acquisition is accomplished in one embodiment by holding the device a few inches from the barcode or data matrix then squeezing the trigger on the "gun". The data carrier is generally easily accessible on the person and in some embodiments it could be removed or positioned for easy reading.

When the trigger is depressed, laser light illuminates the matrix and contrast images corresponding to the location of the cells previously mentioned is reflected back to the gun. In one embodiment the digital information corresponding to the contrast image is relayed to a data processing device containing specific software to convert the digital information to readable text for display on a monitor or to be printed out as a hard copy. The information can also be communicated audibly.

In one embodiment the data processing device, such as a laptop, tablet, computer, or other computing device, powers the scanner "gun" through a cable connecting the gun to a port on the computing device such as a USB port. When the computing device is initially powered up and the scanner is properly connected, a series of beeps can be used to indicate that the scanner is connected and ready for use. Light emitting diodes (LEDs) and other alerting mechanisms can be used to signify that the scanner is ready for use.

Another option is use of a battery-powered gun/scanner that transmits data to the processing hardware via IR, wireless, or other non-discrete technology. The processing hardware can reside in a computing device such as a tablet PC, personal digital assistant (PDA) or similar type computing device that has the wireless connectivity, memory and microcontroller. As previously noted, the system also requires some display or audio/visual mechanism to convey the medical information to the attending medical personnel. The computing device can display the information or otherwise output the data in print or audible means.

As described herein, a further variation is to have the information displayed on the scanner device itself. The scanner can have a microcontroller and decode the encrypted data or the information can be received by the scanner from a computing device. The scanner can have a small display, an audible output and/or a printer mechanism. Another data retrieval mechanism is possible by having the data decoded by a computing device and communicated automatically or manually to the medical personnel via a radio, cellular phone, walkie-talkie or similar device.

If the medical personnel cannot quickly locate a data carrier, the person is checked to determine if there are alternative plans 540 that can be used to obtain medical data about the person. The person can be searched to try to locate medical data or the vehicle may have useful information about the person or an emergency contact may be located. If the emergency personnel are able to determine how such medical data can be obtained 345, then they can obtain certain medical information 550, and the medical professional can finally begin proper treatment 555.

If there is no alternative system for gathering medical information, the emergency responder can attempt to elicit information manually 560 from the distressed person or someone nearby. It may take additional time to process such data 565 and ultimately begin treatment 570.

Speed and prompt care is essential in most emergencies. Delays in trying to retrieve medical information or commencing with medical assistance without medical history can contribute to medical problems.

If there are no easily discernable mechanisms for the retrieval of the medical data, the medical professional can begin the process of manually gathering data or administering treatment without any knowledge of the distressed person.

Figures 6A, 6B:
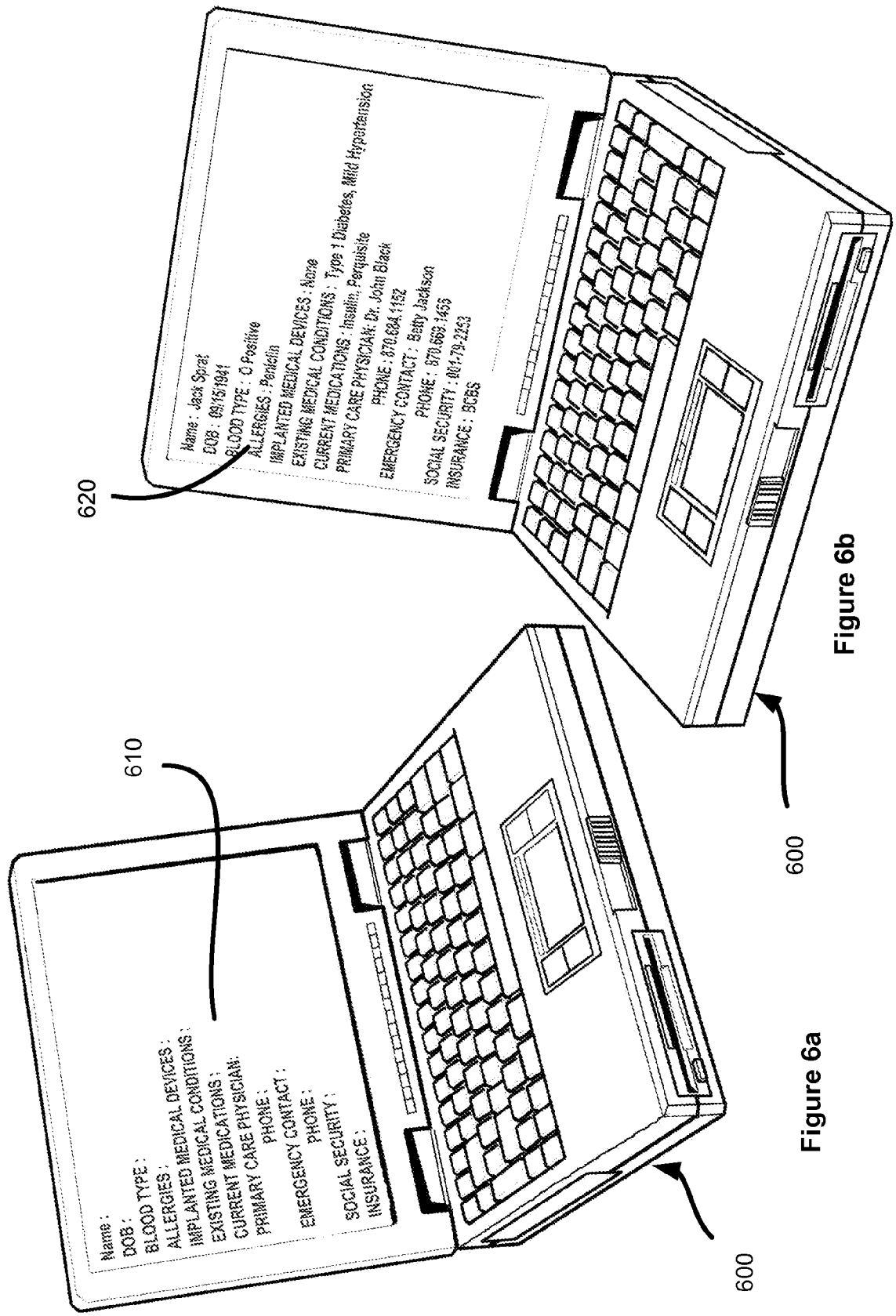
FIG. 6a shows a display screen with a form field that is unpopulated, configured in accordance with one embodiment of the present invention.
FIG. 6b shows a display screen with a populated form field with the data automatically entered from scanning of the data carrier, configured in accordance with one embodiment of the present invention.

FIG. 6a shows a display screen 610 from a computing device 600 with unpopulated data fields including name, contact, blood type, allergies, medications, medical implants, existing medical conditions, primary care physician, emergency contact information, social security number, and insurance provider. Additional and varied information can be easily implemented for particular requirements. FIG. 6b displays the data fields on the display 620 populated after scanning the data carrier and processing the encrypted data. In this particular embodiment, the data reader is wireless and the computing device 600 employs wireless technology to retrieve the encrypted data.

As the data is typically confidential, the system according to one embodiment employs processes that include the generation of encrypted data carriers and implementation of data retrieval or processing using software capable of reading at least some of the encrypted data. The present invention engraves or encodes the information on the data carrier in a manner such that the data can be accurately and easily retrieved and utilized by the personnel. The scanners and associated algorithms for the decoding processing would be limited to authorized individuals.

In the process of encoding the information, the information will also be encrypted to prevent unauthorized retrieval and use of information and can establish access parameters according to a 'need to know' basis. The purpose of this encryption scheme and access is to comply with Privacy Laws and HIPPA regulations, allowing only authorized healthcare providers to access to retrieve certain sensitive information. This also provides the added benefit that a lost or stolen data carrier is rendered useless to unauthorized data retrieval by individuals with criminal intent.

Depending upon the encryption scheme employed, decryption for the data processing portion of the system is required. The data processing software, in addition to the decryption component, can also convert the digital information captured by the scanner into a text file (i.e. ASCII or C40) capable of being displayed in a variety of visual and audio/visual formats such as formatted text display on a computer screen or printed to obtain a hard copy of the information contained in the matrix. Formatting of the readable text display via software allows more variable information to be stored in a similarly sized matrix versus a matrix that contains, for example, field titles, and punctuation.

As noted herein, there are several techniques to establish authorization for the dissemination of the confidential information. One mechanism to establish levels of authorization is to have the software in the system only display authorized fields. Another method is to have the algorithm only process certain data depending upon the authorization. A further embodiment is to have different scanner heads such that a scanner head would only be able to read certain confidential data. Furthermore, the confidential data can be encoded in more than one format or style such that certain scanners would only be able to read certain portions of the data.

Controlled distribution of the decryption software to authorized government and local EMS services, hospitals, clinics, and physician's offices prevents personal information from being illegally obtained by unauthorized parties, thereby instilling client comfort in the overall system. The software would be licensed to authorized parties and employ proper security mechanisms such as passwords and encryption as necessary, and may include biometrics and similar technology to control dissemination of data.

Figure 7:
FIG. 7 shows a handheld computing device with a graphical user display configured in accordance with one embodiment of the invention.

Referring to FIG. 7, a handheld device 700 may include the ability to integrate a scanner or reader 730 into the device, as opposed to the requirement of separate scanning and processing hardware. In this embodiment, the handheld device 700 is a wireless unit that has a power source such as a rechargeable battery, a microprocessor, memory (typically RAM and hard drive), a user interface and some form of display. There are numerous types of devices, such as PDA's and cell phones, having various hardware characteristics and features that can be modified to include certain elements of the present invention.

In one embodiment a scanner head 730 can be integrated into the device 700 so that it can directly read the data carrier. The processing unit can invoke the algorithm stored on the system to unencrypt at least a portion of the read data for which the user has authorization. Control of the device includes using various menu buttons 740 as well as touch screen, keypad, external keyboard, external mouse, and voice commands. Such unencrypted data is then communicated to the end user such as by a display 720 or other audio or audio/visual means.

In another embodiment, the device 700 has a camera 710 that is used to take a picture or image of the encrypted data. The camera may have enhanced imaging to provide sufficient magnification. The device 700 includes OCR processing to identify the symbols and the symbols are then processed with the algorithm to unencrypt the encrypted data. The unencrypted data is then displayed to the authorized user.

For security purposes, the device 700 can employ passwords and/or biometric identification to ensure that only the authorized user is extracting the data. The device 700 can include various known techniques to provide security and authentication. The system may also incorporate various mechanisms to ensure that such unencrypted data is not permanently stored on the unit. A timer, counter or other flag can be used to invoke a delete program to remove certain portions of the data. A further variation is to employ flash memory for storing such data so that information is purged when the unit is turned off.

Also within the scope of the present invention is a scanner unit that simply reads the encrypted data carrier and stores the data into memory. There would be a docking station wherein this scanner unit would couple and download the scanned data for further processing.

Figure 8:
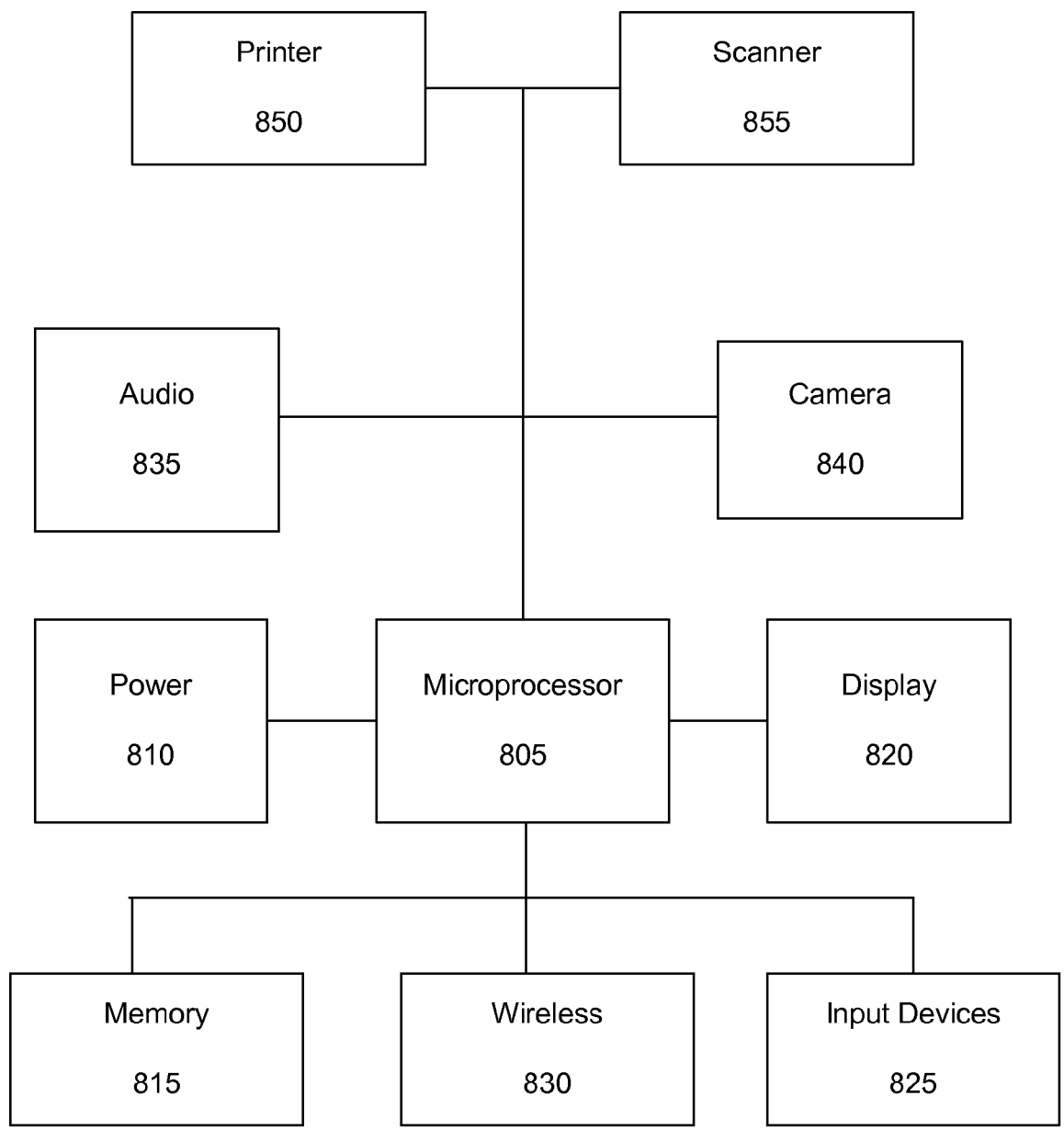
FIG. 8 is a block diagram of a handheld retrieval system according to one embodiment of the invention.

Referring to FIG. 8, a hardware block diagram noting some of the elements of a wireless handheld retrieval system 800 is shown. In this wireless embodiment, there is a microprocessor 805 that controls the various functions and features. A power source 810, typically a rechargeable battery provides power to the microprocessor and other elements that require power. There are one or more input devices 825 for interfacing with the device 800 such as a touchscreen, voice control, keypad and buttons. A mouse and/or external keyboard can be coupled to the device 800 by one of the ports, such as a USB port. The display 820 shows the graphical user interface and can display the various menus and features available to the user for both hardware and software.

There is at least one memory type for the device and may include random access memory (RAM), read only memory (ROM), flash memory, and disk memory. There are some software functions such as operating system and drivers that are required for the system to operate. While some resources require permanent memory, other resources, such as cached Internet webpages only require temporary memory. In one embodiment, certain medical is stored in flash memory such that once the device loses power the information is lost.

The device 800 may further include audio functionality 835 such as providing audio output of data or audio instructions from a doctor. The device may also include a voice recorder to record audio aspects of the event. Such audio information can be saved on the memory or transmitted by the wireless communication 830. A further embodiment includes voice control features such that the user can control certain functions of the device 800 using spoken commands. The speaker and microphone can be integrated within the device and/or have jacks for coupling such components.

A camera 840 can also be incorporated with the device 800 to provide certain additional features. The camera 840 can cooperate with the audio options 835 to provide an audio/video capture. The camera can also be used to capture the scene and/or take pictures or clips of the person to assist in any medical attention. In one embodiment the camera 840 includes sufficient imaging magnification such that it can read nanoengravings/nanoprinting that can be processed by the microprocessor 805 and unencrypted.

As noted herein, the scanner can be integral with the device 800 or separately coupled, however in both cases it would be coupled to the microprocessor 805 in some fashion. A printer can be another peripheral device that can be coupled to the system 800 and allow printing of certain information.

According to one embodiment, the device 800 is able to obtain immediate personal and medical data by processing the encrypted data without having to access a database over a network. The user can then begin treatment and also employ the wireless interface 830 that can provide Internet access, cellular communications and secure access to a network and database. This secondary access to a database may provide additional information about the distressed person. The wireless access also allows the user to communicate with a third party such as doctor, or to look up additional information on the Internet as well as forward messages, data, as well as audio, video, or audio/video information to another person by email or a secure communication channel. The use of secure communication channels is well known in the art and within the scope of the invention.

Another embodiment of the present invention is a system that utilizes existing technology enabling emergency personnel such as Emergency Medical Services (EMS) Technicians to extract required information at the scene of an accident so they may properly care for an injured individual. The distressed person can be unconscious, dazed or unable to provide coherent information. The information may also be obtained in other facilities and situations such as hospitals, walk-in clinics, nursing homes, and private medical practices to retrieve patient information via the external data carrier.

In one aspect, the processing hardware consists of the scanner "gun" and computer system with display mechanism, with an operating system and sufficient system requirements to run software for readable text output. An additional output device such as a printer or audio output is within the scope of the invention.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A system for providing health-related information about a person, comprising:
   a data carrier comprising an existing article of the person and which is coupled about or carried by said person, wherein the existing article has an alerting indication configured for visible coupling about said person;
   a two-dimensional barcode indicative of the health-related information, the barcode being detachably or permanently affixable to the data carrier, wherein the alerting indication is further configured so as to be recognizable to another person as indicating the presence of said barcode; and,
   a microprocessor which is programmed to wirelessly receive information of the barcode optically scanned via a wireless device.

2. The system of claim 1, wherein at least one of the data carrier and the alerting indication is at least affixed to an article of outwardly worn apparel.

3. The system of claim 1, wherein the existing article further has an encrypted data affixed to the existing article.

4. The system of claim 1, wherein said alerting indication comprises an icon or symbol indicative of the presence of the barcode.

5. The system of claim 1, the wireless device comprises a cell phone programmed to detect and recognize said barcode.

6. The system of claim 1 wherein the microprocessor is located at a remote database server provided.

7. The system of claim 1 wherein the barcode is invisible to an observer.

8. A method of providing health-related information about a person, comprising:
   providing a two-dimensional barcode indicative of the health-related information about the person, the barcode being detachably or permanently affixable to an existing article which is coupled about or carried by the person, wherein the existing article has an alerting indication configured for visible coupling about the person so as to be recognizable to another person as indicating the presence of said barcode;
   optically scanning the barcode with a wireless device configured to detect and recognize said barcode;
   processing scanned information from the barcode at a location remote from the wireless device; and
   displaying the health-related information corresponding to the scanned information upon the wireless device.

9. The method of claim 8 wherein providing the alerting indication comprises providing an icon or symbol indicative of the presence of the barcode.

10. The method of claim 8 wherein providing the barcode further comprises providing the barcode which is invisible to an observer.

11. The method of claim 8 wherein optically scanning comprises optically scanning the barcode with a cell phone configured for optical detection.

12. The method of claim 11 wherein processing scanned information comprises wirelessly transmitting the scanned information via the cell phone.

13. The method of claim 11 wherein displaying the health-related information comprises displaying the health-related information upon the cell phone.

\* \* \* \* \*